United States Patent [19]
Kramer et al.

[11] Patent Number: 5,871,468
[45] Date of Patent: Feb. 16, 1999

[54] MEDICAL CATHETER WITH A HIGH PRESSURE/LOW COMPLIANT BALLOON

[75] Inventors: Hans W. Kramer, Temecula; Show-Mean Wu; Ziyun Chen, both of San Diego; Mauricio L. Fugoso, Chula Vista, all of Calif.

[73] Assignee: Medtronic, Inc., Minneapolis, Minn.

[21] Appl. No.: 829,012

[22] Filed: Mar. 31, 1997

Related U.S. Application Data

[63] Continuation-in-part of Ser. No. 637,142, Apr. 24, 1996, abandoned.

[51] Int. Cl.$^6$ .................................................. A61M 29/00
[52] U.S. Cl. .............................. 604/96; 606/194; 264/515
[58] Field of Search ........................ 604/96–103, 104; 264/515; 606/194, 191, 192, 193

[56] References Cited

U.S. PATENT DOCUMENTS

| | | | |
|---|---|---|---|
| Re. 32,983 | 7/1989 | Levy | 428/36.92 |
| Re. 33,561 | 3/1991 | Levy | 428/36.92 |
| 4,020,126 | 4/1977 | Gander et al. | 260/873 |
| 4,250,129 | 2/1981 | Winstead | 264/37 |
| 4,323,071 | 4/1982 | Simpson et al. | 128/343 |
| 4,369,280 | 1/1983 | Dieck et al. | 524/281 |
| 4,413,989 | 11/1983 | Schjeldahl et al. | 604/96 |
| 4,490,421 | 12/1984 | Levy | 428/35 |
| 5,156,612 | 10/1992 | Pinchuk et al. | 606/104 |
| 5,264,260 | 11/1993 | Saab | 428/35.5 |
| 5,270,086 | 12/1993 | Hamlin | 604/96 X |
| 5,306,246 | 4/1994 | Sahatjian et al. | 604/96 |
| 5,328,468 | 7/1994 | Kaneko et al. | |
| 5,344,400 | 9/1994 | Kaneko et al. | |
| 5,344,401 | 9/1994 | Radisch et al. | 604/96 |
| 5,348,538 | 9/1994 | Wang et al. | 604/96 |
| 5,433,713 | 7/1995 | Trotta | 604/264 |
| 5,496,294 | 3/1996 | Hergenrother et al. | 604/282 |
| 5,554,120 | 9/1996 | Chen et al. | 604/96 |
| 5,565,523 | 10/1996 | Chen et al. | 525/176 |
| 5,587,125 | 12/1996 | Roychaudhury | 604/96 X |
| 5,643,209 | 7/1997 | Fugoso et al. | |

FOREIGN PATENT DOCUMENTS

| | | |
|---|---|---|
| 0 135 990 B1 | 9/1990 | European Pat. Off. |
| 0 697 219 A2 | 2/1996 | European Pat. Off. |
| 0 745 395 A2 | 12/1996 | European Pat. Off. |
| 0 747 070 A2 | 12/1996 | European Pat. Off. |
| WO 95/23619 | 9/1985 | WIPO |

OTHER PUBLICATIONS

"Improved Dilatation Catheter Balloons", by Stanley B. Levy, Ph.D., Journal of Clinical Engineering, Jul.–Aug. 1986, pp. 291–296.

*Primary Examiner*—Wynn Wood Coggins
*Assistant Examiner*—N. Kent Gring
*Attorney, Agent, or Firm*—Ann Mueting; Dianne Plunkett Latham; Harold R. Patton

[57] ABSTRACT

A balloon for use in a catheter, wherein the balloon is formed from an aromatic polyester, preferably a blend of a major component comprising an aromatic polyester, and a minor component comprising a compatible secondary thermoplastic semicrystalline polymer having a crystallinity less than that of the aromatic polyester of the major component.

46 Claims, 4 Drawing Sheets

MEDICAL CATHETER WITH A HIGH PRESSURE/LOW COMPLIANT BALLOON

This application is a continuation-in-part of application Ser. No. 08/637,142 filed on Apr. 24, 1996 abandoned.

FIELD OF THE INVENTION

The present invention relates to medical catheters, and more particularly, to high pressure balloons for use in angioplasty catheters.

BACKGROUND OF THE INVENTION

One of the therapeutic procedures applicable to the present invention is known as percutaneous transluminal coronary angioplasty (PTCA). This procedure can be used, for example, to reduce arterial build-up of cholesterol fats or atherosclerotic plaque. Typically a guiding catheter is steered through the vascular system to the site of therapy. A guidewire, for example, can then be advanced through the guiding catheter and a balloon catheter may be advanced within the guiding catheter over the guidewire. The balloon at the distal end of the catheter is inflated causing the site of the stenosis to widen. The original catheter can then be withdrawn and a catheter of a different size or another device such as an atherectomy device can be inserted.

The design of medical devices for insertion into body organs has always involved trading off various performance characteristics in the design of a satisfactory implement. PTCA requires a catheter that is stiff enough to be pushable and go through blockage, while being flexible enough to go around bends. Dilatation balloon catheters commonly have a guidewire lumen pass through the balloon with the balloon and guidewire lumen being bonded at the distal end.

Conventional angioplasty balloons fall into high, medium, and low pressure ranges. Low pressure balloons are those that have burst pressures below 6 atmospheres ($6.1 \times 10^5$ Pascals). Medium pressure balloons are those that have burst pressures between 6 and 12 atm ($6.1 \times 10^5$ and $1.2 \times 10^6$ Pa). High pressure balloons are those that have burst pressures above 12 atm ($1.2 \times 10^6$ Pa). Burst pressure is determined by such factors as wall thickness and tensile strength, for example.

High pressure balloons are desirable because they have the ability to exert more force and crack hard lesions. High pressure balloons are also useful in stent deployment. A biocompatible metal stent props open blocked coronary arteries, keeping them from reclosing after balloon angioplasty. A balloon of appropriate size and pressure is first used to open the lesion. The process is repeated with a stent crimped on a high pressure balloon. The stent is deployed when the balloon is inflated. A high pressure balloon is preferable for stent deployment because the stent must be forced against the artery's interior wall so that it will fully expand thereby precluding the ends of the stent from hanging down into the channel encouraging the formation of thrombus.

High pressure balloon materials are typically stiffer than conventional medium or low pressure balloon materials. Whereas medium or low pressure balloons use materials such as polyethylene, high pressure balloons use materials such as Nylon 12 or polyethylene terephthalate (PET). See, for example, U.S. Pat. No. 4,490,421 (Levy), U.S. Pat. No. Re. 32,983 (Levy), U.S. Pat. No. Re. 33,561 (Levy), and EP 0135990 (Levy), which disclose a high molecular weight, biaxially oriented, flexible, polymeric balloon with a tensile strength of at least 31,714 psi (218.86 MPa), which can be made of PET. See, also, U.S. Pat. No. 5,264,260 (Saab), which discloses a PET balloon, optionally melt blended or mixed with other polymeric or nonpolymeric materials, having an intrinsic viscosity of less than or equal to 0.6 dl/g and a calculated radial tensile strength greater than about 25,000 psi (172 MPa).

Although biaxially oriented PET is advantageous because of its tensile strength, conventional high pressure balloons made only of biaxially oriented PET are very stiff and typically do not have sufficient rewrap such that they can be removed easily after deflation, nor are they sufficiently puncture resistant. Thus, there is a need in the industry for high pressure balloons that have the advantages of biaxially oriented PET, but also display improved rewrap and puncture resistance when compared to balloons made only of PET.

SUMMARY OF THE INVENTION

The above features and advantages of the present invention, as well as others, are accomplished by providing a medical catheter comprising: a catheter body having proximal and distal ends with an outer shaft defining an inflation lumen; an inflatable balloon mounted at the distal end of the catheter body, the balloon being in fluid communication with the inflation lumen and comprising a blend of a major component comprising an aromatic polyester, and a minor component comprising a compatible secondary thermoplastic semicrystalline polymer having a crystallinity less than that of the aromatic polyester of the major component; and the proximal end of the catheter body having an inflation port, the inflation port being in fluid communication with the inflation lumen.

Preferably, the aromatic polyester of the major component and the secondary thermoplastic semicrystalline polymer are chosen such that the balloon has a burst pressure of at least about 16 atm (1.6 MPa) and a radial expansion of no greater than about 0.25 mm from about 6 atm (0.6 MPa) to about 16 atm (1.6 MPa). A particularly preferred example of the aromatic polyester of the major component is a linear aromatic polyester such as polyethylene terephthalate, polyethylene naphthalate, and polybutylene naphthalate. A particularly preferred example of the secondary thermoplastic semicrystalline polymer is an ethylene-vinyl acetate copolymer.

The above features and advantages of the present invention, as well as others, can also be accomplished by providing a medical catheter comprising: a catheter body having proximal and distal ends with an outer shaft defining an inflation lumen; an inflatable balloon mounted at the distal end of the catheter body, the balloon being in fluid communication with the inflation lumen and comprising polyethylene naphthalate; and the proximal end of the catheter body having an inflation port, the inflation port being in fluid communication with the inflation lumen.

The above features and advantages of the present invention, as well as others, can also be accomplished by providing a medical catheter comprising: a catheter body having proximal and distal ends with an outer shaft defining an inflation lumen; an inflatable balloon mounted at the distal end of the catheter body, the balloon being in fluid communication with the inflation lumen and comprising polybutylene naphthalate; and the proximal end of the catheter body having an inflation port, the inflation port being in fluid communication with the inflation lumen.

The present invention also provides a process for making a balloon for use in a catheter. One embodiment of the method includes the steps of: extruding tubing comprising a blend of a major component comprising an aromatic polyester, and a minor component comprising a compatible secondary thermoplastic semicrystalline polymer having a crystallinity less than that of the aromatic polyester of the major component; heating the tubing sufficiently to cause it to flow while stretching it under an appropriate weight to reduce the outer diameter of at least a portion of the tubing, forming pre-necked tubing; and heating the pre-necked tubing sufficiently to cause it to flow while stretching it and substantially simultaneously injecting a gas into the tubing to pressurize it and form a balloon. Preferably, the pre-necked tubing is stretched from both sides at a substantially constant rate of about 60–130 cm/minute for a distance of about 3.5–8.0 cm; and the gas is injected substantially simultaneously at a pressure of at least about 200 psi (1.4 MPa) and a rate of at least about 80 psi/second (0.55 MPa/sec) into the tubing to pressurize it and form a balloon.

Another embodiment of the method includes the steps of: extruding tubing comprising polyethylene naphthalate; heating the tubing sufficiently to cause it to flow while stretching it under an appropriate weight to reduce the outer diameter of at least a portion of the tubing, forming pre-necked tubing; and heating the pre-necked tubing sufficiently to cause it to flow while stretching it and substantially simultaneously injecting a gas into the tubing to pressurize it and form a balloon. Yet another embodiment of the method includes the steps of: extruding tubing comprising polybutylene naphthalate; heating the tubing sufficiently to cause it to flow while stretching it under an appropriate weight to reduce the outer diameter of at least a portion of the tubing, forming pre-necked tubing; and heating the pre-necked tubing sufficiently to cause it to flow while stretching it and substantially simultaneously injecting a gas into the tubing to pressurize it and form a balloon.

DETAILED DESCRIPTION OF THE PREFERRED EMBODIMENTS

The present invention provides a high pressure, low compliance balloon. The balloon of the present invention contains a high molecular weight aromatic polyester, preferably a linear aromatic polyester such as polyethylene terephtalate (PET), polyethylene naphthalate (PEN), and polybutylene naphthalate (PBN), and the like. Preferred embodiments of the balloon of the present invention contain a blend of a major component comprising a high molecular weight aromatic polyester, preferably a linear aromatic polyester such as polyethylene terephthalate, and a minor component comprising a secondary thermoplastic semicrystalline polymer having a crystallinity less than that of the aromatic polyester of the major component. A balloon made from this blend displays improved rewrap and puncture resistant properties when compared to balloons made only of the major component. A balloon made from this blend is also dimensionally stable such that it has good trackability and pushability, it generally retains its size and structural integrity during storage, and, when inflated, it does not substantially expand beyond its formed diameter regardless of internal pressures. Although balloons made from this blend are preferred, balloons made of just PEN or PBN also display many of these desirable properties when compared to balloons made of just PET. Thus, the balloon of the present invention can be used for a variety of applications, particularly high pressure applications, such as stent deployment.

In the blend, the major component comprises an aromatic polyester (e.g., materials derived from an aromatic dicarboxylic acid and an aliphatic glycol) having an intrinsic viscosity of greater than about 0.7 deciliters/gram of material prior to extrusion (measured in a 50:50 mixture of trifluoroacetic acid and dichloromethane at 30 degrees C.), which is a relatively high molecular weight material. It is a thermoplastic, substantially nonelastomeric, semicrystalline polymer containing primarily ester moieties (i.e., a polyester) that is extrudable and orientable. As used herein, a "thermoplastic" polymer is one that is capable of softening when exposed to heat and returning to its original condition when cooled. A "nonelastomeric" polymer is one that is not capable of being stretched to approximately twice its original length and retracting to approximately its original length. A "semicrystalline" polymer is one that displays at least some regular order and some amorphous regions, typically having greater than about 10% amorphous character.

The aromatic polyester is typically a copolymer of an aromatic dicarboxylic acid (or salt thereof) such as terephthalic acid, isophthalic acid, naphthalic acid, etc., and combinations thereof, and a linear, branched, or cyclic aliphatic diol, such as a $(C_2-C_{10})$alkylene glycol (preferably, a $(C_2-C_5)$alkylene glycol), including ethylene glycol, trimethylene glycol, tetramethylene glycol, pentamethylene glycol, hexamethylene glycol, didecamethylene glycol, butanediol, and combinations thereof. Preferred examples of such aromatic polyesters include polyethylene terephthalate, polyethylene naphthalate, polybutylene naphthalate, as well as other such compounds in the naphthalate and terephthalate families. More preferably, the aromatic polyester is polyethylene terephthalate (PET), which is a linear aromatic polyester that is the reaction product of ethylene glycol and terephthalic acid, or polyethylene naphthalate, which is a linear aromatic polyester that is the reaction product of ethylene glycol and naphthalic acid and is available under the trade designations X61 or X90 available from ICI chemicals and Polymers, Fayetteville, N.C.

Preferably, the polyethylene terephthalate used in the blend of the present invention can include other monomers as long as the major portion, and preferably at least about 90%, of the polymer contains the repeating ethylene terephthalate moiety ($-CH_2CH_2)OC(O)-C_6H_4-C(O)O-$). That is, a major portion of the monomers used to prepare PET should be ethylene glycol and terephthalic acid. Other monomers that could be used include other glycols and other dicarboxylic acids. An example of a suitable PET is that commercially available under the trade designation TRAYTUF 1006 from Shell Chemical Co.

In the blend, the minor component comprises a secondary thermoplastic semicrystalline polymer that is compatible with the major component with which it is blended. By this it is meant that the major component does not phase separate during melt processing (e.g., extrusion) from the secondary thermoplastic semicrystalline polymer. This secondary material is a less crystalline material than that of the aromatic polyester of the major component as determined by differential scanning calorimetry or x-ray diffraction. Preferably, it has at least about 5% less crystalline character than the aromatic polyester of the major component, and more preferably at least about 10% less crystalline character. For example, the degree of crystallinity of a sample of ELVAX 470 ethylene-vinyl acetate copolymer is about 15–20%, typically about 17%, whereas the degree of crystallinity of a sample of TRAYTUF 1006 PET is about 60%, as determined by x-ray powder diffraction, as described in greater detail below.

More preferably, the secondary thermoplastic material also has an elastic modulus (i.e., Young's modulus) that is less than that of the aromatic polyester of the major component. Most preferably, both the amount of crystallinity and Young's modulus for the secondary thermoplastic semicrystalline polymer are at least about 5% less than that of the aromatic polyester of the major component. Both the crystalline character (i.e., degree of crystallinity) and the Young's modulus are measured on materials prior to extrusion because extrusion can change the material. For example, a semicrystalline material can be completely changed to an amorphous material upon extrusion.

The secondary thermoplastic semicrystalline polymer may or may not be elastomeric, and preferably, it is substantially nonelastomeric. An "elastomeric" polymer is one that is capable of being stretched to approximately twice its original length and retracting to approximately its original length upon release. The secondary thermoplastic semicrystalline polymer provides flexibility, toughness, and resiliency to the blend of the present invention such that there is improvement in rewrap and puncture resistance of a balloon when blended with an aromatic polyester, particularly PET. This improvement is measured against a balloon made from the same aromatic polyester without the secondary thermoplastic semicrystalline polymer blended therein.

The secondary thermoplastic semicrystalline polymer can be a nonolefinic homopolymer or a copolymer, which is used herein to include terpolymers, tetrapolymers, etc. It can be a copolymer of ethylenically unsaturated monomers including, but not limited to, ethylene, vinyl acetate, fluorinated ethylene, chlorinated ethylene, and combinations thereof, optionally copolymerized with organic acids and esters including methyl acrylate, ethyl acrylate, butylene acrylate, and combinations thereof. If one of the monomers is an olefin, however, at least one of the other monomer or monomers is not an olefin. Such copolymers can be of the AB form or the ABC form. Examples include, but are not limited to, ethylene/ethyl acrylate (EEA), ethylene/methyl acrylate (EMA), ethylene/butylene acrylate (EBA), ethylene vinyl acetate (EVA), ethylene/methyl acrylate/ glycidylmethacrylate (EMA-GMA), ethylene/vinyl acetate/ glycidylmethacrylate (EVA-GMA), ethylene/methyl acrylate/maleic anhydride (EMA-MAH). A preferred example of such a material is that available under the trade designation ELVAX, particularly ELVAX 470, from E. I. Du Pont de Nemours Co., which is a high molecular weight copolymer of ethylene and vinyl acetate. The secondary thermoplastic semicrystalline polymer also can be an aromatic polyester as described above, although this polyester is not as crystalline as the polyester used in the major component. A preferred example of such a material is that available under the trade designation HYTREL, such as HYTREL 4056 and HYTREL 4069, from E. I. DuPont de Nemours Co., which is a block copolymer consisting of a hard (crystalline) segment of polybutylene terephthalate and a soft (amorphous) segment based on long-chain glycols.

Preferably, the secondary thermoplastic semicrystalline polymer is a copolymer of ethylenically unsaturated monomers, such as ethylene and vinyl acetate, which may be polymerized with organic acids. Typically, the ethylene-vinyl acetate (EVA) copolymer includes about 7–40 wt-% vinyl acetate and about 60–93 wt-% ethylene. A sample of ELVAX 470 ethylene-vinyl acetate copolymer has a crystallinity of about 15–20%, typically about 17%, as determined by x-ray crystallography. Depending on the amount of vinyl acetate, the EVA copolymer can vary in crystallinity.

A balloon made from the blend of the present invention includes an amount of the secondary thermoplastic, semicrystalline polymer sufficient to provide improvement in puncture resistance and rewrap when compared to a balloon made with only the aromatic polyester. Typically, the blend includes no greater than about 35 wt-% of the secondary polymer. Preferably, the blend includes about 2–15 wt-% of the secondary polymer. More preferably, the blend includes about 3–7 wt-% of the secondary polymer. Most preferably, the blend includes less than 5 wt-% of the secondary polymer.

Whether made from the blend of the present invention, or just PEN or PBN, the standard balloon size for coronary artery applications is typically within a range of about 5 mm to about 50 mm in length with counterpart balloon diameters ranging from about 1.5 mm to about 5.0 mm in diameter. The minimum burst pressure desired is about 16 atm (1.6 MPa) with an average burst pressure of at least about 20 atm (2.0 MPa). Nominal balloon pressure should be about 6 atm (0.6 MPa) with compliance less than or equal to quarter size (i.e., 0.25 mm) diameter growth from about 6 atm (0.6 MPa) to about 16 atm (1.6 MPa). For example, for a 1.5 mm diameter balloon, the radial expansion (i.e., growth) is 0.019 mm/atm, for a 3.0 mm diameter balloon, the growth is 0.0192 mm/atm, and for a 4.0 mm diameter balloon, the growth is 0.0237 mm/atm. Thus, the radial expansion from about 6 atm (0.6 MPa) to about 16 atm (1.6 MPa) is preferably at least about 6%, and more preferably no greater than about 17%.

Figure 1:
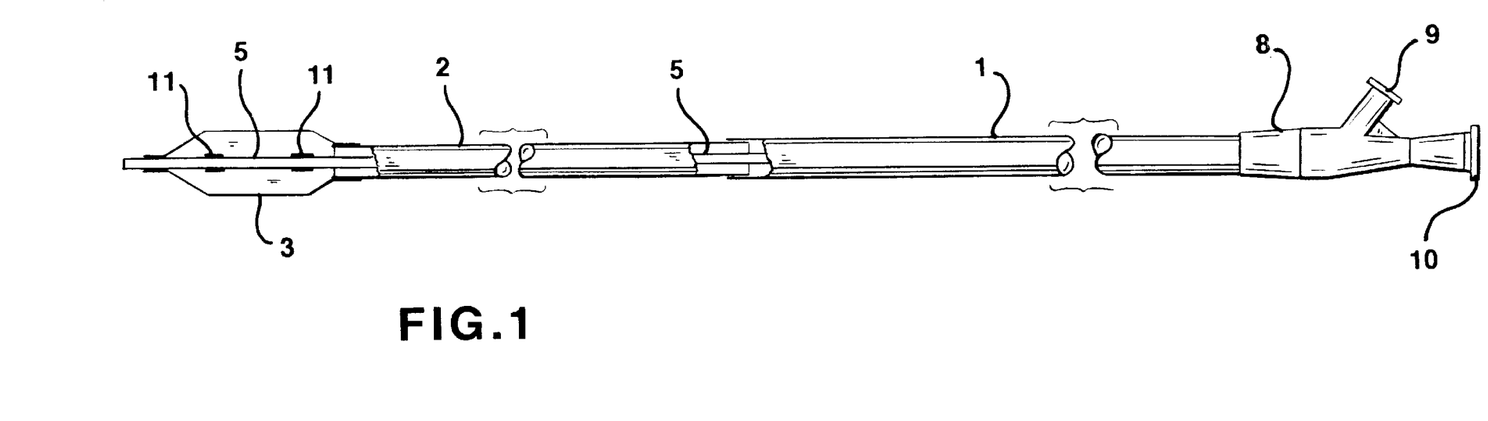
FIG. 1 is a longitudinal view of a catheter with a high pressure balloon of the present invention.

FIG. 1 is a longitudinal view of a high pressure balloon catheter with a co-axial design adapted for use in percutaneous transluminal coronary angioplasty (PTCA). The proximal shaft 1 can be made of polyimide. This increases stiffness with reduced wall thickness and contributes to reduced inflation/deflation times. The distal shaft 2 can be made of 50% high density polyethylene (HDPE) and 50% low density polyethylene (LDPE). The distal shaft 2 is designed to handle at least about 500 psi (3.35 MPa) pressure and still remain flexible enough to navigate torturous paths. The guidewire shaft 5 can be made of HDPE. The distal end of the proximal shaft 1 overlaps the proximal end of the distal shaft 2. Together they form an inflation lumen. The proximal end of distal shaft 2 has a step down 7 (FIG. 3) to receive the distal end of proximal shaft 1. The step down minimizes the transition in outer diameter from the proximal shaft 1 to the distal shaft 2. This is held together by an adhesive 200 (FIG. 3), such as a cyanoacrylate adhesive. FIG. 1 shows how the proximal end of the proximal shaft 1 and the proximal end of the guidewire shaft 5 are affixed to the manifold 8 so that the proximal shaft 1 is in fluid communication with the inflation/deflation port 9. The guidewire shaft 5, in which is located the guidewire 17 (FIG. 2) is in fluid communication with the guidewire port 10.

Figure 2:
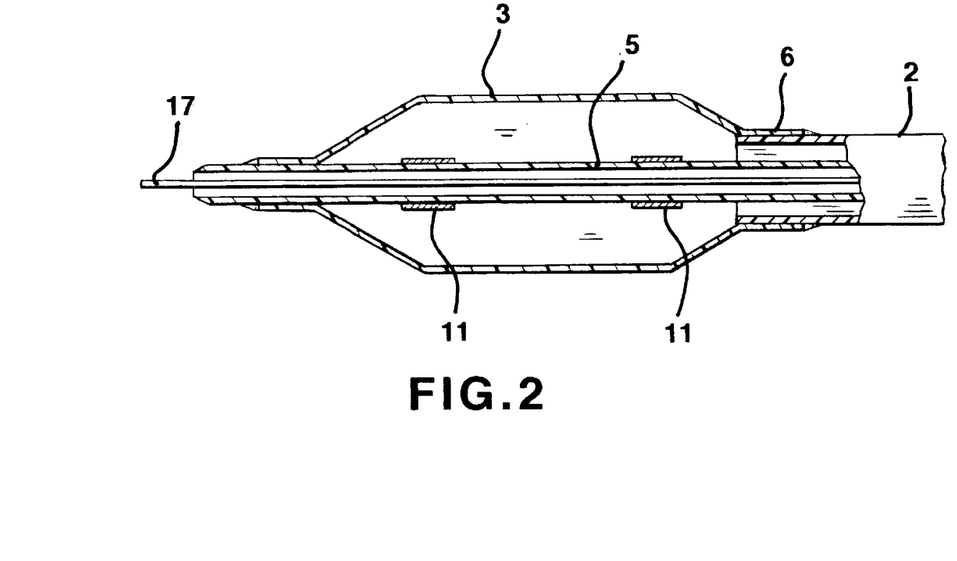
FIG. 2 is an enlargement of the balloon of FIG. 1.
Figure 3:
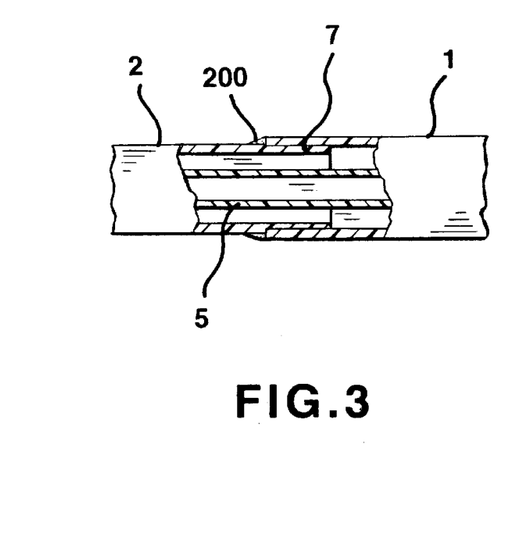
FIG. 3 is a cross-sectional view of the distal shaft of FIG. 1.

FIG. 2 is a cross-sectional view of the balloon 3 portion of FIG. 1. The marker bands 11 are made of two radiopaque tabular tubes bonded with an adhesive, such as a cyanoacrylate adhesive. These can be made of platinum material of about 1.5 mm in length and are positioned about 0.5 mm from the balloon cones and bonded with an adhesive, such as a cyanoacrylate adhesive, on the guidewire shaft 5. The balloon proximal tail 6 is about 3 mm in length and is bonded with an adhesive, such as an ultraviolet curable adhesive, to the distal end of distal shaft 2.

Figure 4:
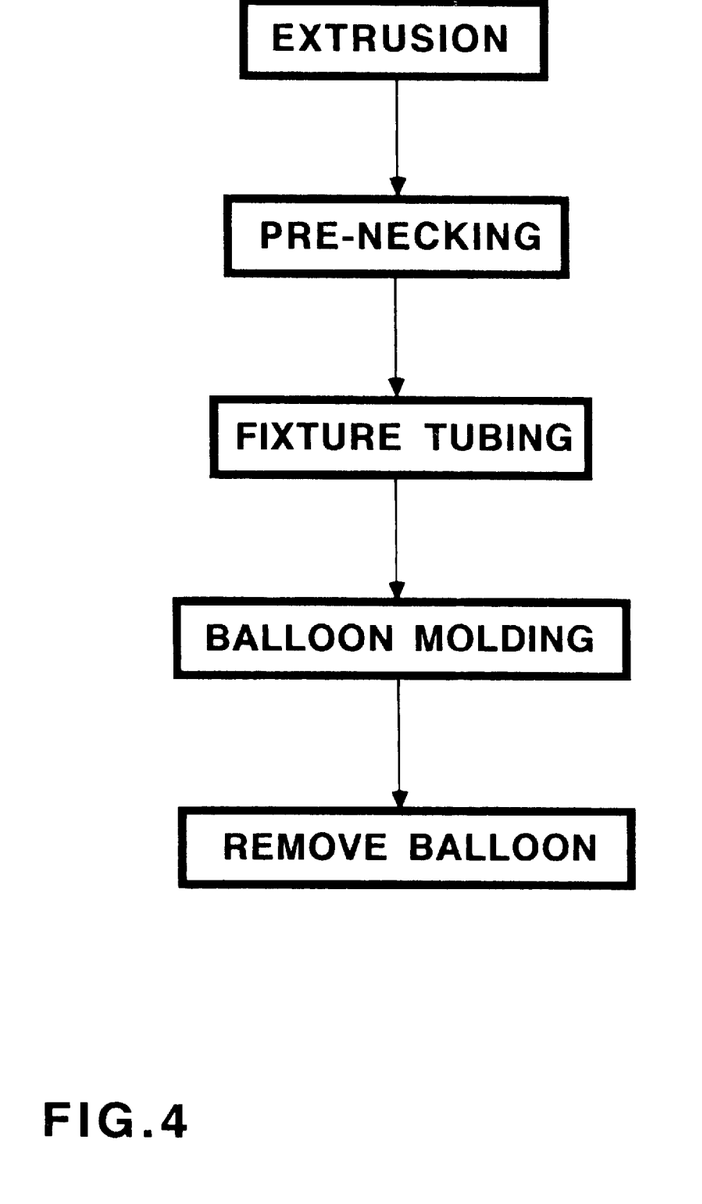
FIG. 4 is a schematic of the overall balloon forming process of the present invention.

The balloon of the present invention can be made by a method that involves forming a tube and expanding the tube to form a balloon, as well as orienting the polymer, preferably biaxially orienting the polymer. Referring to FIG. 4, preferably, the process involves extruding the blend (or just PEN or PBN) into the form of a tube; drawing the tubing to both orient the polymer and reduce the thickness of the tubing in a pre-necking apparatus; placing the tubing in a balloon molding apparatus (i.e., fixturing the tubing); stretching and expanding the tubing to further orient the polymer and form a balloon in the molding apparatus; and removing the balloon from the balloon molding apparatus. Although this is a preferred method, conventional methods can be used as well to make balloons from the blend (or just PEN or PBN).

Figure 5:
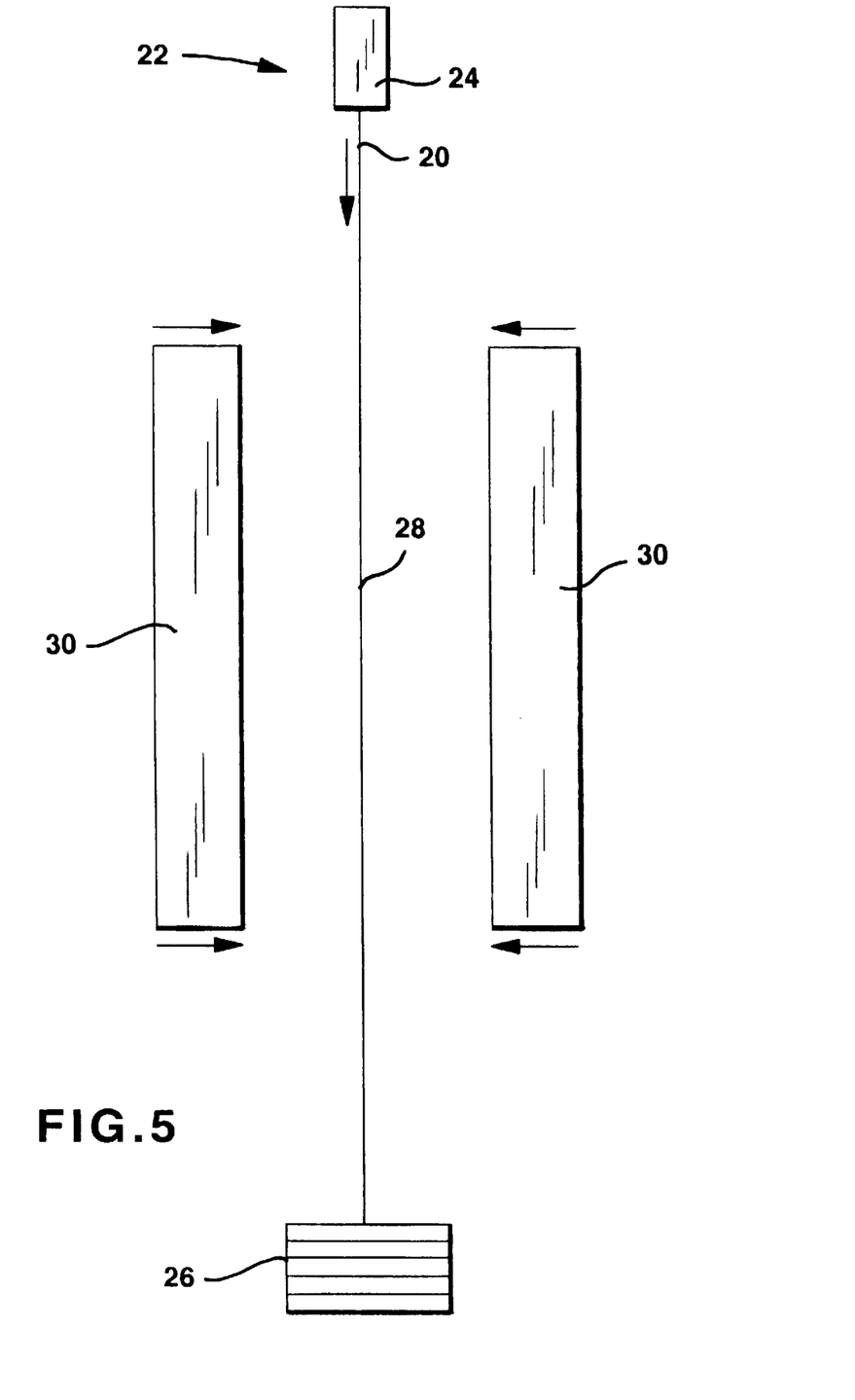
FIG. 5 is a schematic of the pre-necking apparatus used in the balloon forming process of the present invention.

Standard techniques of processing, e.g., extruding, the blend (or just the PEN or PBN) into the form of a tube are used. These techniques are well known to one of skill in the art. Once the tube is formed, it is preferably placed in a pre-necking apparatus, which is represented by FIG. 5, although this pre-necking step is not required. One end of the tubing 20 is placed in the pre-necking apparatus 22 at clamp 24, which is designed to clamp around the outside of the tubing while keeping the tube open, and the other end is attached to a weight 26. The tubing 20 is placed in the apparatus 22 vertically with the tubing hanging freely with a constant weight 26 placed on the end. The size of the weight 26 is determined to provide the desired amount of material in the necked region 28. For example, for a 5 wt-% ethylene-vinyl acetate blend with PET, a 75 gram weight is used for 4.0 mm and 3.0 mm tubing, a 50 gram weight for 2.0 and 2.5 mm tubing, and a 43 gram weight for 1.5 mm tubing. The weight 26 on the end of the tubing 20 will generally vary depending on the composition of the blend and the desired properties of the balloon, and can be determined by one of skill in the art. The tubing 22 is then heated using block heaters 30 to soften the polymer blend and cause it to flow, thereby causing the tubing to be subsequently stretched and oriented by the weight. This temperature of the block heaters 30 is typically within a range of about 90–150 degrees C., preferably about 90–120 degrees C. for blends containing PET, 120–150 degrees C. for PEN, and 115–145 degrees C. for blends containing PEN, and more preferably about 93–113 degrees C. for 5 wt-% ethylene-vinyl acetate (EVA) blend with PET. This temperature can vary depending on the composition of the blend and the desired properties of the balloon, and can be determined by one of skill in the art. For example, for the 5 wt-% EVA-PET blend, the temperature is set at about 135 degrees C. The necking occurs in a very short period of time, typically on the order of seconds. For example, for a 5 wt-% ethylene-vinyl acetate blend with PET, the 4.0 mm tubing is stretched for about 12 seconds, the 3.0 mm tubing for about 9 seconds, and the 2.0 and 1.5 mm tubing for about 8 seconds.

The inside diameter of the tubing does not significantly change during this pre-necking step of the process, however, the outside diameter is reduced, at least for part of the tubing. This results in a two-step tube, which is also referred to herein as necked tubing. For example, after necking the 5 wt-% ethylene-vinyl acetate blend with PET using the above-described conditions, a 4.0 mm tubing typically has a 0.043 inch (0.109 cm) outside diameter at one end and a 0.025 inch (0.064 cm) outside diameter at the other end. This pre-necking step provides for a material with reduced mass at one end, which provides for a reduced profile at that end of the balloon as well as improved flexibility and rewrap. During the next stage of the process wherein the balloon is actually formed, the thin end of the tubing becomes the distal end of the balloon and the thicker end becomes the balloon main body and the proximal end of the balloon. Thus, the thinner end is used at the tip or front end of the catheter (i.e., the leading end of the catheter when inserted into the vascular system).

Figure 6:
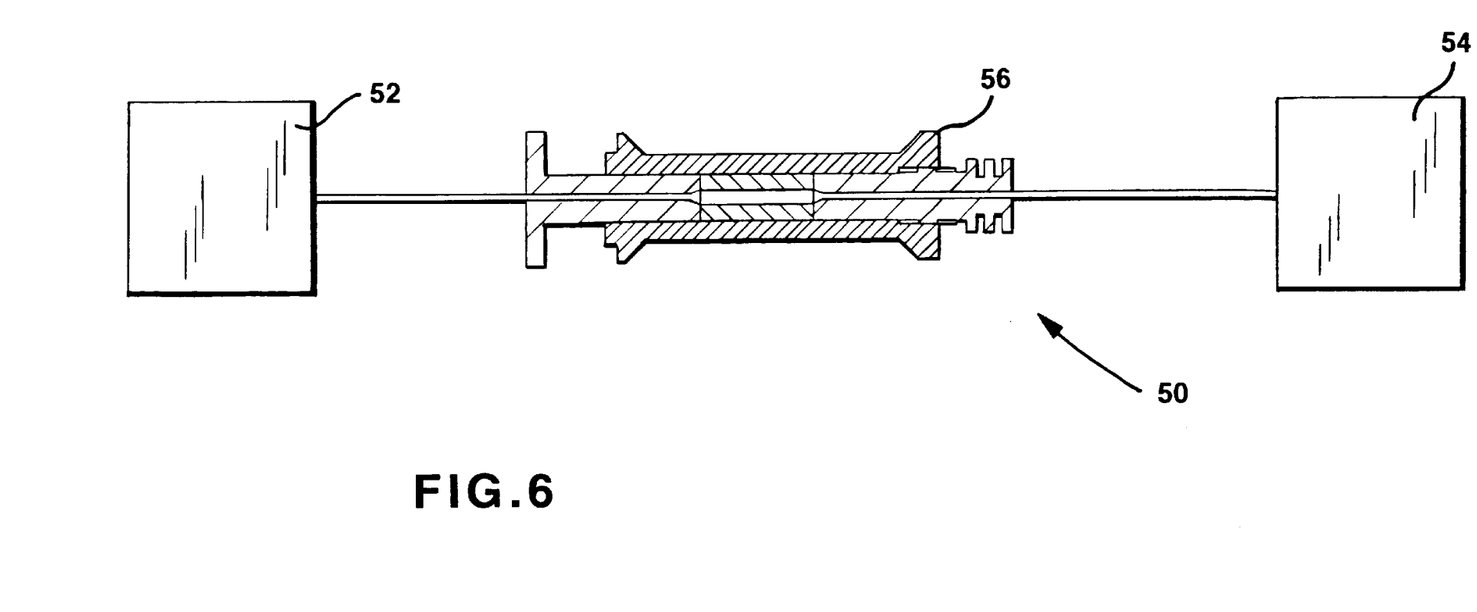
FIG. 6 is a schematic of the balloon molding apparatus used in the balloon forming process of the present invention.

Referring to FIG. 6, the pre-necked balloon tubing is positioned horizontally in the molding apparatus 50, which has tension control at both sides using clamps 52 and 54 to keep the tubing under constant tension during the heating and stretching stage of the process. While the tubing is in the molding apparatus 50, it is heated by steam in the mold chamber 56 to a preset temperature that allows for further stretching of the tubing and orienting of the polymer. This temperature is typically within a range of about 90–150 degrees C. preferably about 90–120 degrees C. for blends containing PET, 120–150 degrees C. for PEN and 115–145 degrees C. for blends containing PEN, and more preferably about 93–113 degrees C. for 5 wt-% ethylene-vinyl acetate (EVA) blend with PET. This temperature can vary depending on the composition of the blend and the desired properties of the balloon, and can be determined by one of skill in the art. For example, for the 5 wt-% EVA-PET blend, the temperature is set at about 111 degrees C. for 4.0 mm tubing, 106 degrees C. for 3.0 mm tubing, and 102 degrees C. for 2.0 mm and 1.5 mm tubing. For PEN, the temperature is set at about 149 degrees C. for 4 mm tubing. For a 5 wt-% EVA-PEN blend or a 5 wt-% HYTREL-PEN blend, the temperature is set at about 143 degrees C.

The heated tubing is immediately stretched at a substantially constant rate, preferably from both sides, for a specific distance, although different rates can be used for each end of the tubing. At substantially the same time, a gas such as nitrogen is injected at a controlled rate, which is relatively fast, and at a preset pressure, which is relatively high, into the tubing to form the balloon. The balloon is formed substantially immediately upon injection of the gas. Thus, there is a need for very rapid injection of the gas. The combination of the mold temperature and the stretching rate and distance determine the balloon's neck dimensions. These parameters are chosen such that the distal end of the balloon has a smaller outside diameter, smaller inside diameter, and smaller wall thickness than the proximal end of the balloon. This provides advantage when the distal end is used as the front end or leading end of the balloon. Thus, the processing conditions contribute to the determination of the balloon profile and stiffness, which are important for trackability and pushability of a catheter.

Typically, the rate of stretching is within a range of about 60–130 cm/minute, preferably about 63–127 cm/minute, the distance stretched is within a range of about 3.5–8.0 cm, preferably about 3.8–7.6 cm. The distance stretched can be equal on each end of the tubing, or it can vary. For example, tubing can be stretched about 2.5 cm on one side and about 5.0 cm on the other. The rate of gas injection is at least about 80 psi/second (0.55 MPa/sec), preferably within a range of about 120–300 psi/second (0.83–2.1 MPa), and more preferably at about 140 psi/second (0.97 MPa). The gas pressure is at least about 200 psi (1.4 MPa), preferably within a range of about 270–350 psi (1.9–2.4 MPa), and more preferably at about 280 psi (1.9 MPa) for PET-containing blends, or 310 psi (2.1 MPa) for PEN or PEN-containing blends. Typically, the smaller the balloon size, the faster the rate of stretching is needed, which in turn requires a faster rate of gas injection. These conditions can vary depending on the composition of the blend and the desired properties of the balloon, and can be determined by one of skill in the art. For example, for the 5 wt-% EVA-PET blend using the temperature listed above, a 4.0 mm tubing is typically stretched for about 1.8 inches (4.6 cm) at a rate of about 25 inches/minute (53.5 cm/min), a 3.0 mm tubing is typically stretched for about 2.0 inches (5.1 cm) at a rate of about 38 inches/minute (96.5 cm/min), a 2.0 mm tubing is typically stretched for about 2.5 inches (6.4 cm) at a rate of about 37 inches/minute (94.0 cm/min), and a 1.5 mm tubing is typically stretched for about 2.8 inches (7.1 cm) at a rate of about 47 inches/minute (119.4 cm/min). For PEN using the temperature listed above, a 4.0 mm tubing is typically stretched for about 2.5 inches (6.4 cm) at a rate of about 20 inches/minute.

The balloon mold is then preferably heated to a temperature effective to stabilize the balloon structure by further crystallizing the polymer. This step is important for control of the balloon growth rate (i.e., balloon compliance and final burst strength). Typically, this is within a range of about 137–155 degrees C., and preferably within a range of about 143–149 degrees C. The balloon is then held at this temperature at a preferably high pressure (e.g., 280 psi) for up to about 12 seconds. The balloon mold is then cooled by evacuating the steam and introducing water until the mold reaches a temperature of about 21–27 degrees C. The balloon is then removed from this fixture and ready for placement on a catheter.

X-Ray Powder Diffraction Procedure for Analysis of Degree of Crystallinity

Powder and pellet samples are packed into a deep cavity holder. Films are placed on a zero background glass slide to avoid amorphous contributions from the substrate. The sample is placed on a holder of the diffractometer and scanned from 4–40 degrees, or appropriate two-theta range at 2 degrees/minute speed and 0.03 step size, using Copper K-alpha radiation (1.54 angstrom wavelength). The slits are set at 1 degree divergence slit, 1 degree scatter slit, 0.3 degree anti-scatter slit, and 0.15 degree receiving slit. The two-theta positions and intensities of each observed peak are marked. The two-theta values are then converted to interatomic distanced or "d" spacing using the well-known Bragg Equation.

The degree of crystallinity is normally calculated by taking the ratio of the area under crystalline peaks to the total area. However, peaks are usually not symmetrical, the background line is uncertain, and the shape of the noncrystalline peak or peaks may change as the polymer becomes more crystalline. For these reasons, a method that gives a "relative" percent crystallinity is often used. The background line is drawn between two points chosen so that all diffraction patterns for this sample have minima at these points. The noncrystalline peak is sketched in, based on a set of minimum points. The ratio of the area under the crystalline peaks and above the noncrystalline peak to the total area above the background line, multiplied by 100, is taken as a relative percent crystallinity.

The preceding specific embodiments are illustrative of the practice of the invention. It is to be understood, however, that other expedients known to those skilled in the art or disclosed herein, may be employed without departing from the scope of the appended claims.

What is claimed is:

1. A medical catheter comprising:
   (a) a catheter body having proximal and distal ends with an outer shaft defining an inflation lumen;
   (b) an inflatable balloon mounted at the distal end of the catheter body, the balloon being in fluid communication with the inflation lumen and comprising a blend of:
       (i) a major component comprising an aromatic polyester; and
       (ii) less than 5 wt-% of a minor component comprising a compatible secondary thermoplastic semicrystalline polymer having a crystallinity less than that of the aromatic polyester of the major component; and
   (c) the proximal end of the catheter body having an inflation port, the inflation port being in fluid communication with the inflation lumen.

2. The medical catheter of claim 1 wherein the aromatic polyester has an intrinsic viscosity of greater than about 0.7 deciliters/gram.

3. The medical catheter of claim 1 wherein the aromatic polyester is polyethylene terephthalate, polyethylene naphthalate, or polybutylene naphthalate.

4. The medical catheter of claim 3 wherein the aromatic polyester is polyethylene terephthalate.

5. The medical catheter of claim 3 wherein the aromatic polyester is polyethylene naphthalate.

6. The medical catheter of claim 3 wherein the aromatic polyester is polybutylene naphthalate.

7. The medical catheter of claim 1 wherein the secondary thermoplastic semicrystalline polymer has a crystallinity at least about 5% less than that of aromatic polyester of the major component.

8. The medical catheter of claim 1 wherein the secondary thermoplastic semicrystalline polymer is substantially non-elastomeric.

9. The medical catheter of claim 8 wherein the secondary thermoplastic semicrystalline polymer is an ethylene-vinyl acetate copolymer.

10. The medical catheter of claim 1 wherein the aromatic polyester of the major component and the secondary thermoplastic semicrystalline polymer are chosen such that the balloon has a burst pressure of at least about 16 atm (1.6 MPa) and a radial expansion of no greater than about 0.25 mm from about 6 atm (0.6 MPa) to about 16 atm (0.6–1.6 MPa).

11. The medical catheter of claim 1 wherein the secondary thermoplastic semicrystalline polymer is a block copolymer comprising a hard segment of polybutylene terephthalate and a soft segment based on long-chain glycols.

12. A medical catheter comprising:
   (a) a catheter body having proximal and distal ends with an outer shaft defining an inflation lumen;
   (b) an inflatable balloon mounted at the distal end of the catheter body, the balloon being in fluid communication with the inflation lumen and comprising a blend of:
       (i) a major component comprising polyethylene terephthalate; and
       (ii) less than 5 wt-% of a minor component comprising an ethylene-vinyl acetate copolymer; and
   (c) the proximal end of the catheter body having an inflation port, the inflation port being in fluid communication with the inflation lumen.

13. The medical catheter of claim 12 wherein the polyethylene terephthalate has an intrinsic viscosity of greater than about 0.7 deciliters/gram.

14. A method for making a balloon catheter, comprising:

(a) extruding tubing comprising a blend of:
  (i) a major component comprising an aromatic polyester; and
  (ii) a minor component comprising a compatible secondary thermoplastic semicrystalline polymer having a crystallinity less than that of the aromatic polyester of the major component;
(b) heating the tubing sufficiently to cause it to flow while stretching it under an appropriate weight to reduce the outer diameter of at least a portion of the tubing, forming pre-necked tubing; and
(c) heating the pre-necked tubing sufficiently to cause it to flow while stretching it and substantially simultaneously injecting a gas into the tubing to pressurize it and form a balloon.

15. The method of claim 14 wherein the portion of the pre-necked tubing with the reduced outer diameter forms the distal end of the tubing for placement on the front end of the catheter.

16. The method of claim 14 wherein the tubing is heated to a temperature of about 90–120 degrees C. in the pre-necking step.

17. The method of claim 14 wherein the tubing is heated to a temperature of about 90–120 degrees C. in the balloon-forming step.

18. The method of claim 14 further including a step of heating the balloon to a temperature effective to further crystallize the polymer blend.

19. The method of claim 18 wherein the step of heating the pre-necked tubing comprises:
  (a) stretching it from both sides at a substantially constant rate of about 60–130 cm/minute for a distance of about 3.5–8.0 cm; and
  (b) substantially simultaneously injecting a gas at a pressure of at least about 200 psi (1.4 MPa) and a rate of at least about 80 psi/second (0.55 MPa/sec) into the tubing to pressurize it and form a balloon.

20. The method of claim 14 wherein the step of heating the pre-necked tubing comprises:
  (a) stretching it from both sides at a substantially constant rate of about 60–130 cm/minute for a distance of about 3.5–8.0 cm; and
  (b) substantially simultaneously injecting a gas at a pressure of at least about 200 psi (1.4 MPa) and a rate of at least about 80 psi/second (0.55 MPa/sec) into the tubing to pressurize it and form a balloon.

21. A method for making a balloon catheter, comprising:
  (a) extruding tubing comprising a polymer blend comprising polyethylene naphthalate and a secondary thermoplastic polymer;
  (b) heating the tubing sufficiently to cause it to flow while stretching it under an appropriate weight to reduce the outer diameter of at least a portion of the tubing, forming pre-necked tubing; and
  (c) heating the pre-necked tubing sufficiently to cause it to flow while stretching it and substantially simultaneously injecting a gas into the tubing to pressurize it and form a balloon.

22. The method of claim 21 wherein the step of heating the pre-necked tubing comprises:
  (a) stretching it from both sides at a substantially constant rate of about 60–130 cm/minute for a distance of about 3.5–8.0 cm; and
  (b) substantially simultaneously injecting a gas at a pressure of at least about 200 psi (1.4 MPa) and a rate of at least about 80 psi/second (0.55 MPa/sec) into the tubing to pressurize it and form a balloon.

23. The method of claim 21 wherein the secondary thermoplastic semicrystalline polymer has a crystallinity at least about 5% less than that of polyethylene naphthalate.

24. The method of claim 23 wherein the secondary thermoplastic semicrystalline polymer is substantially non-elastomeric.

25. The method of claim 24 wherein the secondary thermoplastic semicrystalline polymer is an ethylene vinyl acetate copolymer.

26. The method of claim 21 wherein the secondary thermoplastic polymer is a compatible secondary thermoplastic semicrystalline polymer having a crystallinity less than that of the polyethylene naphthalate.

27. The method of claim 21 wherein the balloon has a burst pressure of at least about 16 atm (1.6 MPa) and a radial expansion of no greater than about 0.25 mm from about 6 atm (0.6 MPa) to about 16 atm (0.6–1.6 MPa).

28. A method for making a balloon catheter, comprising:
  (a) extruding tubing comprising a polymer blend comprising polybutylene naphthalate and a secondary thermoplastic polymer;
  (b) heating the tubing sufficiently to cause it to flow while stretching it under an appropriate weight to reduce the outer diameter of at least a portion of the tubing, forming pre-necked tubing; and
  (c) heating the pre-necked tubing sufficiently to cause it to flow while stretching it and substantially simultaneously injecting a gas into the tubing to pressurize it and form a balloon.

29. The method of claim 28 wherein the step of heating the pre-necked tubing comprises:
  (a) stretching it from both sides at a substantially constant rate of about 60–130 cm/minute for a distance of about 3.5–8.0 cm; and
  (b) substantially simultaneously injecting a gas at a pressure of at least about 200 psi (1.4 MPa) and a rate of at least about 80 psi/second (0.55 MPa/sec) into the tubing to pressurize it and form a balloon.

30. The method of claim 28 wherein the secondary thermoplastic polymer is a compatible secondary thermoplastic semicrystalline polymer having a crystallinity less than that of the polybutylene naphthalate.

31. The method of claim 30 wherein the secondary thermoplastic semicrystalline polymer has a crystallinity at least about 5% less than that of polybutylene naphthalate.

32. The method of claim 31 wherein the secondary thermoplastic semicrystalline polymer is substantially non-elastomeric.

33. The method of claim 32 wherein the secondary thermoplastic semicrystalline polymer is an ethylene vinyl acetate copolymer.

34. The method of claim 28 wherein the balloon has a burst pressure of at least about 16 atm (1.6 MPa) and a radial expansion of no greater than about 0.25 mm from about 6 atm (0.6 MPa) to about 16 atm (0.6–1.6 MPa).

35. A medical catheter comprising:
  (a) a catheter body having proximal and distal ends with an outer shaft defining an inflation lumen;
  (b) an inflatable balloon mounted at the distal end of the catheter body, the balloon being in fluid communication with the inflation lumen and comprising a polymer blend comprising polyethylene naphthalate; and
  (c) the proximal end of the catheter body having an inflation port, the inflation port being in fluid communication with the inflation lumen;

wherein the polymer blend further comprises a compatible secondary thermoplastic semicrystalline polymer having a crystallinity less than that of the polyethylene naphthalate.

36. The medical catheter of claim 35 wherein the secondary thermoplastic semicrystalline polymer has a crystallinity at least about 5% less than that of polyethylene naphthalate.

37. The medical catheter of claim 36 wherein the secondary thermoplastic semicrystalline polymer is substantially nonelastomeric.

38. The medical catheter of claim 37 wherein the secondary thermoplastic semicrystalline polymer is an ethylene vinyl acetate copolymer.

39. A medical catheter comprising:
(a) a catheter body having proximal and distal ends with an outer shaft defining an inflation lumen;
(b) an inflatable balloon mounted at the distal end of the catheter body, the balloon being in fluid communication with the inflation lumen and comprising a polymer blend comprising polyethylene naphthalate; and
(c) the proximal end of the catheter body having an inflation port, the inflation port being in fluid communication with the inflation lumen;
wherein the balloon has a burst pressure of at least about 16 atm (1.6 MPa) and a radial expansion of no greater than about 0.25 mm from about 6 atm (0.6 MPa) to about 16 atm (0.6–1.6 Mpa).

40. A medical catheter comprising:
(a) a catheter body having proximal and distal ends with an outer shaft defining an inflation lumen;
(b) an inflatable balloon mounted at the distal end of the catheter body, the balloon being in fluid communication with the inflation lumen and comprising a polymer blend comprising polybutylene naphthalate; and
(c) the proximal end of the catheter body having an inflation port, the inflation port being in fluid communication with the inflation lumen;
wherein the polymer blend further comprises a compatible secondary thermoplastic semicrystalline polymer having a crystallinity less than that of the polybutylene naphthalate.

41. The medical catheter of claim 40 wherein the secondary thermoplastic semicrystalline polymer has a crystallinity at least about 5% less than that of polybutylene naphthalate.

42. The medical catheter of claim 41 wherein the secondary thermoplastic semicrystalline polymer is substantially nonelastomeric.

43. The medical catheter of claim 42 wherein the secondary thermoplastic semicrystalline polymer is an ethylene vinyl acetate copolymer.

44. A medical catheter comprising:
(a) a catheter body having proximal and distal ends with an outer shaft defining an inflation lumen;
(b) an inflatable balloon mounted at the distal end of the catheter body, the balloon being in fluid communication with the inflation lumen and comprising a polymer blend comprising polybutylene naphthalate; and
(c) the proximal end of the catheter body having an inflation port, the inflation port being in fluid communication with the inflation lumen;
wherein the balloon has a burst pressure of at least about 16 atm (1.6 MPa) and a radial expansion of no greater than about 0.25 mm from about 6 atm (0.6 MPa) to about 16 atm (0.6–1.6 Mpa).

45. A medical catheter comprising:
(a) a catheter body having proximal and distal ends with an outer shaft defining an inflation lumen;
(b) an inflatable balloon mounted at the distal end of the catheter body, the balloon being in fluid communication with the inflation lumen and comprising a single layer comprising a blend comprising polyethylene naphthalate and a secondary thermoplastic polymer; and
(c) the proximal end of the catheter body having an inflation port, the inflation port being in fluid communication with the inflation lumen.

46. A medical catheter comprising:
(a) a catheter body having proximal and distal ends with an outer shaft defining an inflation lumen;
(b) an inflatable balloon mounted at the distal end of the catheter body, the balloon being in fluid communication with the inflation lumen and comprising a single layer comprising a blend comprising polybutylene naphthalate and a secondary thermoplastic polymer; and
(c) the proximal end of the catheter body having an inflation port, the inflation port being in fluid communication with the inflation lumen.

* * * * *